United States Patent
Kawashima et al.

[11] Patent Number: 6,146,592
[45] Date of Patent: *Nov. 14, 2000

[54] AUTOMATIC BIOCHEMICAL ANALYZER

[75] Inventors: Kiyoshi Kawashima; Shin Saito; Akio Kimura, all of Tokyo; Minoru Inatsugu, Saitama; Saburo Yoshimi, Tokyo, all of Japan

[73] Assignee: JEOL Ltd., Tokyo, Japan

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/916,090

[22] Filed: Aug. 21, 1997

[51] Int. Cl.[7] .................................................. G01N 35/10
[52] U.S. Cl. ................................ 422/67; 422/64; 436/43; 436/47; 436/49; 436/50; 436/179; 436/180
[58] Field of Search ............................... 422/63, 64, 67; 436/43, 47, 48, 49, 50, 179, 180

[56] References Cited

U.S. PATENT DOCUMENTS

| | | | |
|---|---|---|---|
| 5,679,309 | 10/1997 | Bell | 422/67 |
| 5,741,461 | 4/1998 | Takahashi et al. | 422/67 |
| 5,773,662 | 6/1998 | Imai et al. | 436/50 |
| 5,789,252 | 8/1998 | Fujita et al. | 436/49 |
| 5,876,668 | 3/1999 | Kawashima et al. | 422/64 |

FOREIGN PATENT DOCUMENTS

5-2024  of 1993  Japan.

*Primary Examiner*—Long V. Le
*Attorney, Agent, or Firm*—Webb Ziesenheim Logsdon Orkin & Hanson, P. C.

[57] ABSTRACT

There is disclosed an automatic biochemical analyzer having a sample turntable and a reaction turntable. Plural sample containers for holding samples are arrayed on the sample turntable. Plural reaction containers are arrayed on the reaction turntable. A sampling pipette draws in a sample from some sampling container and injects the sample into some reaction container. A reagent pipette draws in some reagent from some reagent container and injects the reagent into the same reaction container. The resulting mixture is stirred by a stirring device. Produced reaction products are detected by a detector. Let N be the number of the reaction containers on the reaction turntable. The reaction turntable is rotated in M pitches in one step. Note that M and N do not have any common factor. First and second injecting positions adjacent to each other are established as positions where the reagent pipette can inject a reagent into the reaction container in position. First and second stirring positions adjacent to each other are established as positions where the stirring device can stir liquids in the reaction container in position. The stirring device can be moved between the first and second stirring positions. Thus, one reagent pipette can be used for two kinds of reagents. Also, one stirring device can be used for two kinds of reagents.

8 Claims, 5 Drawing Sheets

AUTOMATIC BIOCHEMICAL ANALYZER

FIELD OF THE INVENTION

The present invention relates to an automatic biochemical analyzer for analyzing biological samples such as blood and urine in terms of plural items.

BACKGROUND OF THE INVENTION

Such automatic biochemical analyzers for analyzing biological samples have been known, as proposed in Japanese Patent Laid-Open No. 2024/1993. In this prior art technique, a plurality of sample containers are set on a sample disk. In this instrument, aliquots of sample in the sample containers set on the sample disk are drawn in by a sample pipette and dispensed into reaction containers on a reaction disk. A reagent pipette draws in reagents from plural reagent disks and adds the reagents to the aliquots of sample. Thus, the sample is analyzed in terms of plural items. During the analysis, the order in which the items are analyzed is determined, taking account of the time required for the processing, in order to shorten this processing time.

In this automatic biochemical analyzer, plural kinds (e.g., four kinds) of reagents are successively added to a biological sample in each reaction container on the reaction turntable. The induced reactions are optically detected. The added reagents are referred to first through fourth reagents, respectively, according to the order in which they are added. Whenever each kind of reagent is put into a reaction container, it is necessary to stir the mixture inside the container.

Providing a reagent pipette and a stirring device for each different kind of reagent may also be conceivable. That is, four sets of reagent pipettes and stirring devices corresponding to the first through fourth reagents are arranged around the reaction turntable. However, the sample pipette for pipetting the sample into the reaction containers, a washing device for washing the sample pipette, a detector, a washing device for washing the reaction containers, and so on are disposed around the reaction turntable. Therefore, limitations are imposed on the space where those reagent pipettes and stirring devices are installed. Consequently, it is very difficult to dispose as many as four sets of reagent pipettes and stirring devices around the reaction turntable.

SUMMARY OF THE INVENTION

In view of the foregoing circumstances, the present invention has been made.

It is an object of the present invention to provide an automatic biochemical analyzer equipped with less reagent pipettes and less stirring devices.

This object is achieved in accordance with the teachings of he invention by an automatic biochemical analyzer comprising: a sample turntable on which a plurality of sample containers for holding samples are arrayed; a reaction turntable on which a plurality of reaction containers for holding reagents are substantially regularly spaced from each other by one pitch circumferentially; a sampling pipette for drawing in an aliquot of sample from a selected one of said sample containers and injecting the drawn aliquot of sample into a selected one of the reaction containers; a reagent pipette for drawing in an aliquot of a selected one of said reagents and injecting the drawn aliquot of reagent into said selected reaction container at any one of first and second injecting positions adjacent to each other; a stirring device for stirring said sample aliquot and said reagent aliquot in said selected reaction container at any one of first and second stirring positions adjacent to each other; and a detector for detecting reaction products arising from said sample aliquot after the stirring. Let N be the number of the sample containers on the reaction turntable. The reaction turntable is rotated in M pitches in one step. The M and N are so selected that they do not have any common factor. The stirring device is capable of moving between said first and second stirring positions.

Other objects and features of the invention will appear in the course of the description thereof, which follows.

DETAILED DESCRIPTION OF THE INVENTION

Figure 1:
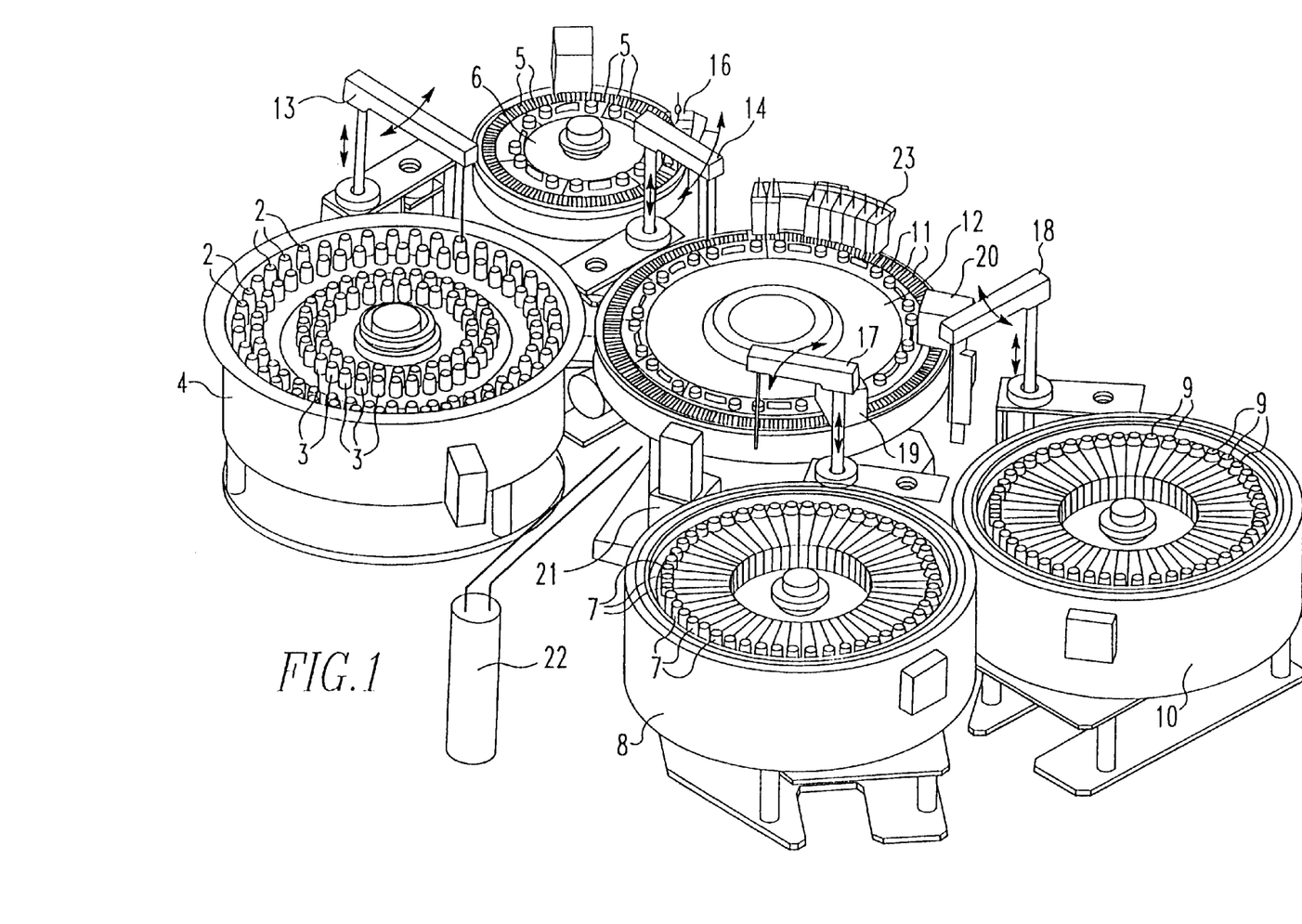
FIG. 1 is a perspective view of an automatic biochemical analyzer in accordance with the present invention.

The whole structure of an automatic biochemical analyzer in accordance with the present invention is shown in FIG. 1. The biochemical analyzer, generally indicated by reference numeral 1, comprises a sample turntable 4, a diluting turntable 6, a first reagent turntable 8, a second reagent turntable 10, and a reaction turntable 12. A given number of sample containers 2 holding biological samples are set on the sample turntable 4. The samples are drawn from the sample containers 2 and diluted. The diluted samples are put in diluting containers 5, which in turn are set on the diluting turntable 6. Reagent containers 7 holding first and fourth reagents of different kinds are set on the reagent turntable 8. Reagent containers 9 holding second and third reagents of different kinds are set on the second reagent turntable 10. A given number of reaction containers 11 are set on the reaction turntable 12.

On the sample turntable 4, the sample containers 2 are arranged in two rows and regularly spaced from each other by one pitch. Each row consists of 42 sample containers 2. This sample turntable 4 is rotated incrementally, one pitch at a time.

A diluting pipette 13 is mounted between the sample turntable 4 and the diluting turntable 6 and reciprocated between the sample turntable 4 and the diluting turntable 6 by a drive mechanism (not shown). The diluting pipette 13 is moved up and down for aspirating and injecting operations. When the diluting pipette 13 gains access to one sample container 2 in a given location on the sample turntable 4, a sampling pump (not shown) is operated to take in a given amount of sample. Then, the diluting pipette 13 obtains access to one diluting container 5 in a given position on the diluting turntable 6. A given amount of diluent (normally physiological salt solution) supplied from the diluting pipette 13 itself is injected into the diluting container 5, along with the sample. As a result, the sample is diluted by a given factor within the diluting container 5. Thereafter, the diluting pipette 13 is washed by a washing device (not shown) located at the midway location in the reciprocating stroke of the pipette.

A sampling pipette 14, a stirring device 15, and a washing device 16 are mounted around the diluting turntable 6, as well as the diluting pipette 13. The diluted sample in the diluting container 5 is stirred by the stirring device 15, thus producing a uniform diluted sample. Let N be the number of the diluting containers 5 circumferentially arranged on the diluting turntable 6. The diluting turntable 6 is rotated incrementally, M pitches at a time. To arrange these devices 13, 14, 15, and 16 with sufficient degrees of freedom, M and N are so selected as not to have any common factor.

A drive mechanism (not shown) reciprocates the sampling pipette 14 between the diluting turntable 6 and the reaction turntable 12 through the dilution washing device 16. When the sampling pipette 14 is lowered to gain access to one diluting container 5 in a given position on the diluting turntable 6, a diluting sampling pump (not shown) is operated to drawn in a given amount of diluted sample. Then, the sampling pipette 14 is lowered to obtain access to one reaction container 11 in a given position on the reaction turntable 12, and the pipette 14 injects the drawn diluted sample into the reaction container 11.

The stirring device 15 is moved up and down by a vertical driving mechanism (not shown) and has a stirring rod (not shown) reciprocating diametrically of the diluting turntable 6. The stirring rod of the diluting turntable 6 advances into a diluted sample in the diluting container 5 and moves back and forth to produce a uniform diluted sample. The washing device 16 cleanses the sampling pipette 14 after the diluted sample is injected into the reaction container 11.

Disposed around the reaction turntable 12 are reagent pipettes 17, 18, stirring devices 19, 20, a multi-wavelength photometer 21 acting as a detector, a thermostatic chamber 22, and a washing device 23 for washing the reaction container, as well as the sampling pipette 14. These devices operate at their respective positions relative to the reaction container 11.

Figure 2:
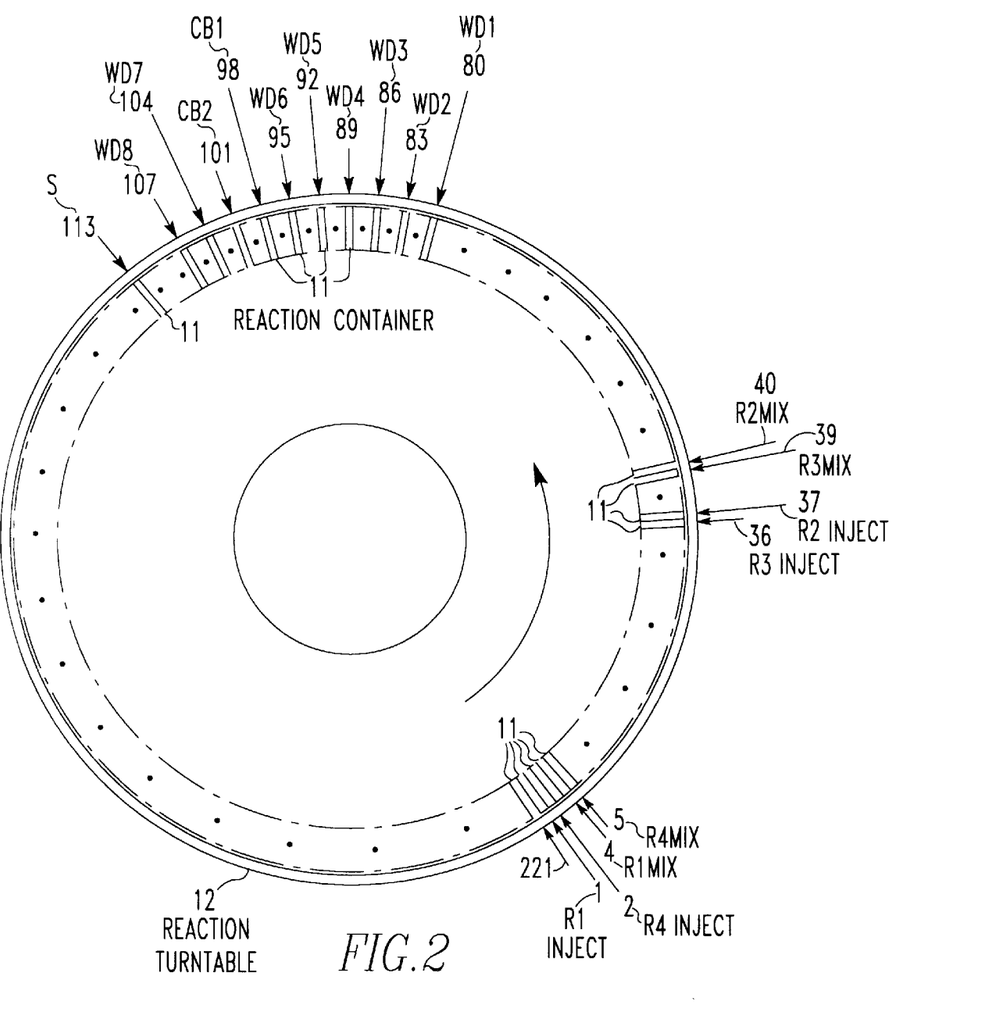
FIG. 2 is a top plan view of a reaction turntable used in the analyzer shown in FIG. 1, illustrating various operation positions.

Referring to FIG. 2, it is assumed that 221 reaction containers 11 are disposed along the whole outer periphery of the reaction turntable 12. Numerals 1 through 221 are given to 221 positions taken in a counterclockwise direction along the outer surface of the reaction turntable 12. A first reagent is injected at position 1. A fourth reagent is injected at position 2. The first reagent is stirred at position 4. The fourth reagent is stirred at position 5. A third reagent is injected at position 36. A second reagent is injected at position 37. The third reagent is stirred at position 39. The second reagent is stirred at position 40. The reaction container 11 is washed and checked for contamination at positions 80–107. A diluted sample is injected at position 113. The pipettes 14, 17, 18, the stirring devices 19, 20, and the washing device 23 perform their operations on the reaction container 11 halted at the positions described above.

The reagent pipette 17 is reciprocated between the reaction turntable 12 and the reagent turntable 8 by a driving mechanism (not shown). When the first reagent should be pipetted into the reaction container 11, the reagent pipette 17 is lowered and obtains access to the reagent container 7 located at a given position on the reagent turntable 8. Then, a reagent pump (not shown) is operated to draw in a given amount of reagent. Thereafter, the pipette rotates toward the reaction turntable 12. The pipette is lowered to get access to the reaction container 11 positioned at a given location on the reaction turntable 12. The drawn reagent is injected as the first reagent into the reaction container 11.

The reagent pipette 17 operates similarly when the fourth reagent held in other reagent container 7 is pipetted into the reaction container 11. As mentioned previously, the position at which the fourth reagent is pipetted differs from the position at which the first reagent is pipetted. That is, the reagent pipette 17 is designed so that it can come to a halt at two pipetting positions.

The stirring device 19 is moved up and down by a driving mechanism (not shown) and has a stirring rod (not shown) that is rotated and moved back and forth. The stirring rod is advanced into the reaction container 11 in a given position on the reaction turntable 12 and then rotated and moved back and forth diametrically of the reaction turntable 12. This assures that the first reagent induces a uniform reaction of the diluted sample.

The stirring device 19 similarly stirs the diluted sample and the fourth reagent inside the reaction container 11. As described above, the position at which the fourth reagent is stirred is different from the position at which the first reagent is stirred.

The reagent pipette 18 draws the second or third reagent from the second reagent turntable 10 and injects the drawn reagent into the reaction container located in a given position on the reaction turntable, in exactly the same way as the reagent pipette 17. The stirring device 20 stirs the second or third reagent and the diluted sample in the reaction container, in exactly the same manner as the stirring device 19.

The multi-wavelength photometer 21 measures the absorbance of the diluted sample inside the reaction container 11 and detects the reaction products arising from the diluted sample in the reaction container 11.

The thermostatic chamber 22 maintains constant the temperature of the reaction containers 11 on the reaction turntable 12 at all times.

The washing device 23 uses a draining pump (not shown) to draw in the detected diluted sample and reagent held in the reaction container 11. The drawn sample and reagent are discharged into a draining tank. Then, a detergent pump (not shown) supplies a detergent into this reaction container 11 to wash the interior of the reaction container 11. The detergent is then drawn off into the draining tank. At this time, the degree of contamination of the reaction container 11 is measured. If it is heavily contaminated, a warning is issued to replace the container.

Let N be the number of the reaction containers 11 circumferentially arranged on the reaction turntable 12. This reaction turntable 12 is rotated incrementally, M pitches at a time. To arrange these devices 14, 17, 18, 19, 20, 21, 22, and 23 with sufficient degrees of freedom, M and N are so selected as not to have any common factor. The reaction turntable 12 is rotated through more than 180 degrees in one step. In the present embodiment, the 221 reaction containers 11 are rotated in 112 pitches in one step.

Suppose that one reaction container is halted at position 1. This container is rotated in 112 pitches in the next one step and reaches position 113. The container is rotated in 112 pitches in the next one step and arrives at position 4. In summary, after incremental movements in two steps, the container has been moved in 3 pitches.

Figure 3:
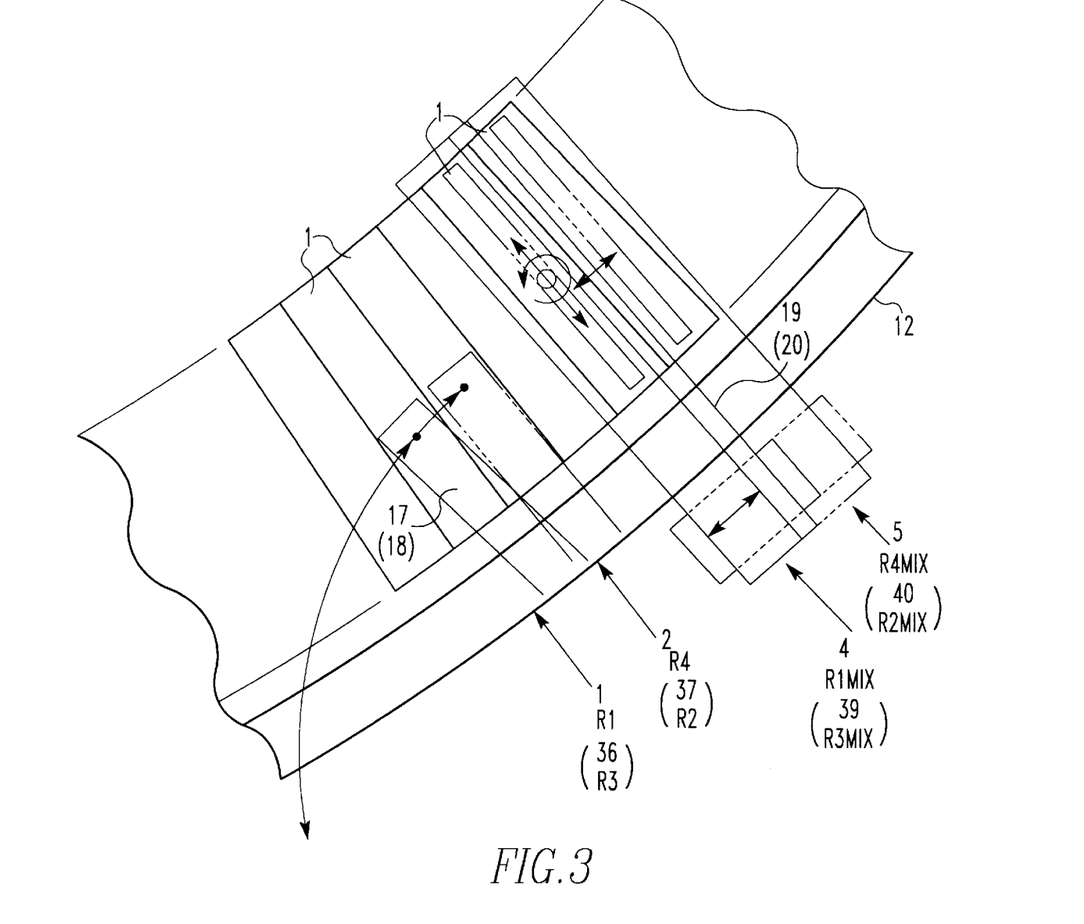
FIG. 3 is a fragmentary schematic enlarged view of a reagent pipette 17 and a stirring device 19 shown in FIG. 1.

FIG. 3 is a fragmentary schematic enlarged view of the reagent pipette 17 and the stirring device 19 of the analyzer shown in FIG. 1. The reagent pipette 17 is rotated along a trajectory indicated by an arc in FIG. 3. This pipette 17 can be halted either at position 1 or at position 2 by selecting the angle through which the pipette rotates at a time. In position 1, the reagent pipette 17 can pipette a first reagent into the reaction container 11. In position 2, the reagent pipette 17 can inject a fourth reagent into the reaction container 11.

On the other hand, the stirring device 19 can move one pitch (i.e., the distance between the successive reaction containers 11) straightly between positions 4 and 5 along a straight line tangent to the outer surface of the reaction turntable 12. The stirring device 19 may also move in a slightly curved path along the outer surface of the reaction turntable 12. The reagent pipette 18 and stirring device 20 that are put in parentheses in FIG. 3 are constructed similarly to the reagent pipette 17 and stirring device 19, respectively, shown in FIG. 3.

Figure 5A:
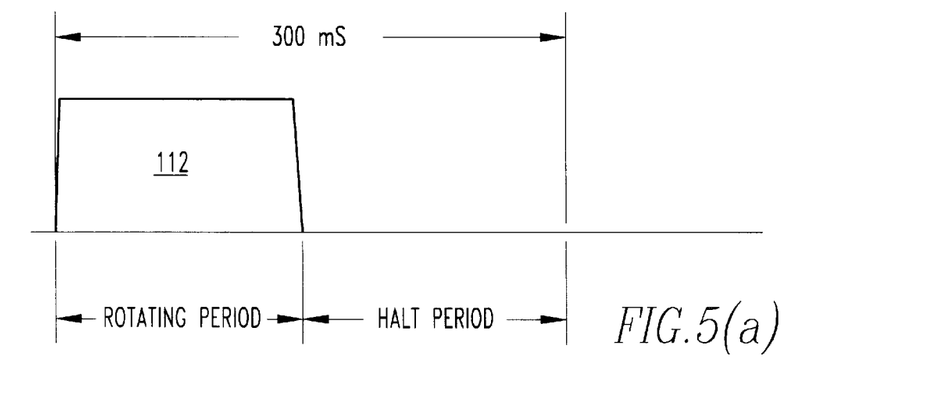
FIG. 5(a) is a diagram illustrating the intervals at which a sequence of operations illustrated in Table I is repeated.
Figure 5B:
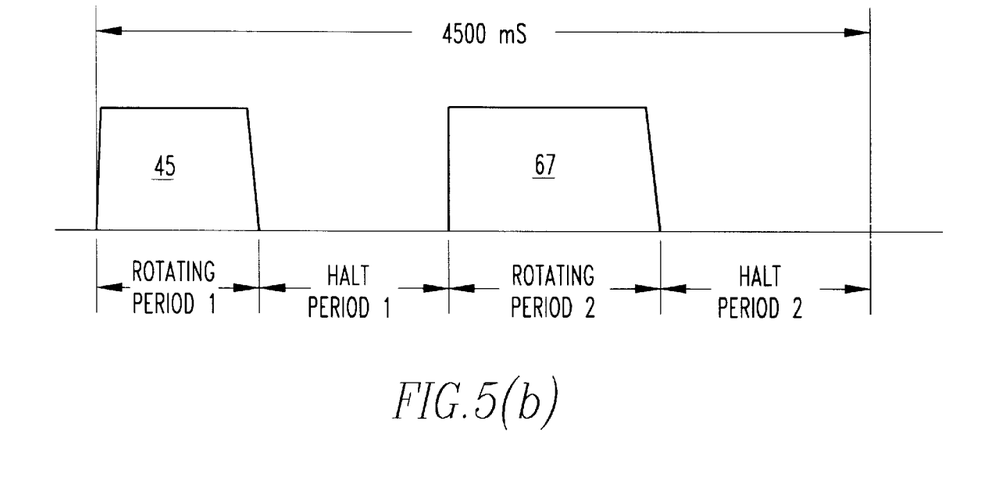
FIG. 5(b) is a diagram illustrating the intervals at which a sequence of operations illustrated in Table II is repeated.

The present example of reagent-injecting-and-stirring device constructed in this way performs various operations on one reaction container at the timing illustrated in Table I. As the reaction turntable 12 is rotated in one step, each reaction container 11 is rotated in M pitches (e.g., 112 pitches). M does not have any common factor with the total number, or 221, of the reaction containers 11. Furthermore, M is in excess of half of the total number. Whenever the reaction turntable 12 rotates in one step, the turntable rotates in 112 pitches and comes to a halt. This series of operations is repeated at intervals of 3 seconds, as shown in FIG. 5(a). During the former half of the 3-second period, the reaction turntable is rotated. During the latter half, the turntable is halted, and a set of operations is performed. One sequence of operations is completed in 221 steps in 3 seconds×221.

In Table I, some steps (e.g., steps 1, 2, and 3) each have an upper column and a lower column. The upper column indicates a position assumed before rotation, while the lower column indicates a position taken after rotation. The remaining steps each have one column indicating a position taken before rotation.

In Table I, in step 1, some reaction container 11A comes to a halt at position 1 after rotation of the reaction turntable. The reagent pipette 17 gains access to this reaction container 11A. A first reagent previously aspirated is injected into the container 11A (R1) (see FIG. 3). At this time, any diluted sample is not yet injected into the reaction container 11A.

In step 2, the reaction turntable 12 rotates in 112 pitches. The reaction container 11A into which the first reagent was pipetted at position 1 is halted at a diluted sample-injecting position 113.

The sampling pipette 14 gets access to the reaction container 11A and pipettes a diluted sample into the reaction container 11A (S). In particular, a nozzle (not shown) mounted at the front end of the sampling pipette 14 is advanced into the first reagent. Under this condition, the diluted sample is injected into the first reagent. Then, the nozzle is withdrawn from the first reagent. At this time, a slight amount of the first reagent adheres to the outer surface of the nozzle at the front end. Since the amount of the first reagent is greater than the amount of the diluted sample, the adhesion of the first reagent hardly affects the reaction of the diluted sample with the first reagent.

In step 3, the reaction turntable 12 is rotated in 112 pitches and comes to a halt. During the rotation, the reaction container 11A passes in front of the multi-wavelength photometer 21, which in turn measures the absorbance of the mixture of the diluted sample and the reagent inside the reaction container 11A. Whenever the reaction container 11A subsequently passes in front of the photometer 21 during rotation of the reaction turntable in this way, the photometer 21 performs a similar measurement.

During this halt, the reaction container 11A arrives at a first stirring position 4 (FIG. 3). The stirring device 19 stirs the diluted sample and the first reagent in the reaction container 11A (R1MIX). The stirring rod of the stirring device 19 is lowered into the diluted sample and first reagent in the container 11A. The stirring rod is rotated and reciprocated back and forth diametrically of the reaction turntable 12. The rotation and reciprocating movement of the stirring rod, done longitudinally of the reaction container, make the stirring operation efficient.

In step 4, the reaction turntable 12 is rotated in 112 pitches and comes to a halt. The reaction container 11A having the first reagent already stirred in step 3 is at position 116. At this time, the reaction container 11A is not processed at all. In this way, the reaction turntable 12 is rotated in 112 pitches, brought to a halt, and stirring is done in a sequence of steps in 3 seconds, for example. This sequence of steps is repeated at regular intervals.

In step 25, the reaction turntable 12 comes to a halt, and the reaction container 11A arrives at a second reagent-injecting position 37 (FIG. 3). The reagent pipette 18 injects the second reagent in the same way as the injection of the first reagent (R2).

In step 27, the reaction turntable 12 comes to a halt, and the reaction container 11A comes to a halt at the second stirring position 40. The stirring device (20) stirs the second reagent (R2MIX) in the same way as the stirring (R1MIX) of the first reagent by the stirring device 19.

In step 98, the reaction turntable 12 comes to a halt, and the reaction container 11A arrives at a third reagent-injecting position (36). Since this third reagent-injecting position (36) is adjacent to the second reagent-injecting position (37), the reagent pipette (18) is rotated to this third reagent-injecting position, and then the reagent pipette (18) (R3) injects the third reagent.

In step 100, the reaction turntable 12 comes to a halt, and the reaction container 11A reaches a third stirring position (39) adjacent to the second stirring position (40). The stirring device (20) is rotated in one pitch up to the third stirring position along a straight line tangent to the outer surface of the reaction turntable 12. At this location, the stirring device 20 stirs the third reagent (R3MIX).

In step 149, the reaction turntable 12 comes to a halt, and the reaction container 11A reaches a fourth reagent-injecting position 2 (FIG. 3) adjacent to the first reagent-injecting position 1. The reagent pipette 17 is rotated to this fourth reagent-injecting position and then injects the fourth reagent (R4).

In step 151, the reaction turntable 12 comes to a halt, and the reaction container 11A arrives at the fourth stirring position 5 adjacent to the first stirring position 4. The stirring device 19 is moved one pitch straight along the straight line tangent to the outer surface of the reaction turntable 12 and assumes a state indicated by the phantom lines in FIG. 2. Then, the stirring device 19 can stir the fourth reagent (R4MIX).

As mentioned previously, whenever the reaction container 11A passes in front of the multi-wavelength photometer 21 during rotation of the reaction turntable 12, the photometer 21 detects reaction products arising from the diluted sample in response to each reagent. These measurements end before step 201. Then, the reaction container 11A used for measurements is washed. More specifically, a cleaning device 23 washes the reaction container 11A (WD1, WD2, WD3, WD4, WD5, and WD6), using an alkaline detergent, an acidic detergent, or pure water, at positions 80, 83, 86, 89, 92, and 95, respectively, in steps 201, 203, 205, 207, 209, and 211, respectively.

In steps 214 and 216, the degree of contamination of each reaction container 11 is measured, using physiological salt solution at positions 98 and 101, respectively. Finally, in steps 217 and 219, the cleaning device 23 discharges liquid from the reaction container 11 at positions 104 and 107, respectively. In this way, the measurement of the sample in one reaction container 11A is completed. In practice, reaction containers successively moved into position 1 subsequently to the reaction container 11A are treated similarly at intervals of one step.

In this way, in the present invention, the reaction turntable 12 is rotated in 112 pitches in one step. It is to be noted that 112 does not have any common factor with the total number, or 221, of the reaction containers 11. This increases the degrees of freedom in designing the instrument. As a result, the two positions at which two kinds of reagents are pipetted or stirred can be made adjacent to each other around the reaction turntable. Consequently, four kinds of reagents can be pipetted and stirred by two reagent pipettes and two stirring devices. Hence, the instrument can be made up of less number of components than heretofore. Also, the cost can be curtailed.

Table II illustrates an example of timing of a sequence of operations performed on one reaction container in the same manner as in the example of Table I. The turntable is rotated in 112 pitches in one step similarly to the example of Table I but the period of the 112 pitches is divided into a former operative period corresponding to earlier 45 pitches and a latter operative period corresponding to latter 67 pitches. Two halt periods are placed between these two operative periods. An operation can be carried out during each halt period. The total period consisting of the two operative periods and the two halt periods is set, for example, to 4.5 seconds. The control mechanism for operating the instrument at the timing illustrated in Table II is the same as the control mechanism of FIG. 1.

In this embodiment, as the reaction turntable 12 is rotated one revolution in 221 steps, one reaction container 11 brought to a halt at position 1 in step 1 is again halted at position 1 in step 193. The reaction container 11 halted at position 2 in step 119 is again brought to a halt at position 2 in step 149. The reaction container 11 halted at position 4 in step 3 is again halted at position 4 in step 195. The reaction container 11 halted at position 5 in step 121 is again halted at position 5 in step 151.

That is, while the reaction turntable 12 is being rotated in 221 steps, the same reaction container 11 is halted twice at the same position. Therefore, when the same reaction container 11 halts at position 1 twice and at position 2 twice, it is possible to pipette four kinds of reagents with one reagent pipette 17. Also, when the same reaction container 11 halts at position 4 twice and at position 5 twice, four stirring steps can be performed with one stirring device 19. Similarly, four kinds of reagents can be pipetted with another reagent pipette 18. Also, four stirring steps can be carried out with another stirring device 20. Accordingly, in the present example of timing of injection and stirring of reagents, 8 kinds of reagents, in total, can be injected and stirred with two reagent pipettes 17, 18 and two stirring devices 19, 20.

In this manner, more reagents can be injected and stirred with less reagent pipettes and less stirring devices by variously establishing the stepwise movements of the reaction turntable. This greatly increases the degrees of freedom in designing the instrument. This embodiment yields the same advantages as the above-described embodiment.

Figure 4:
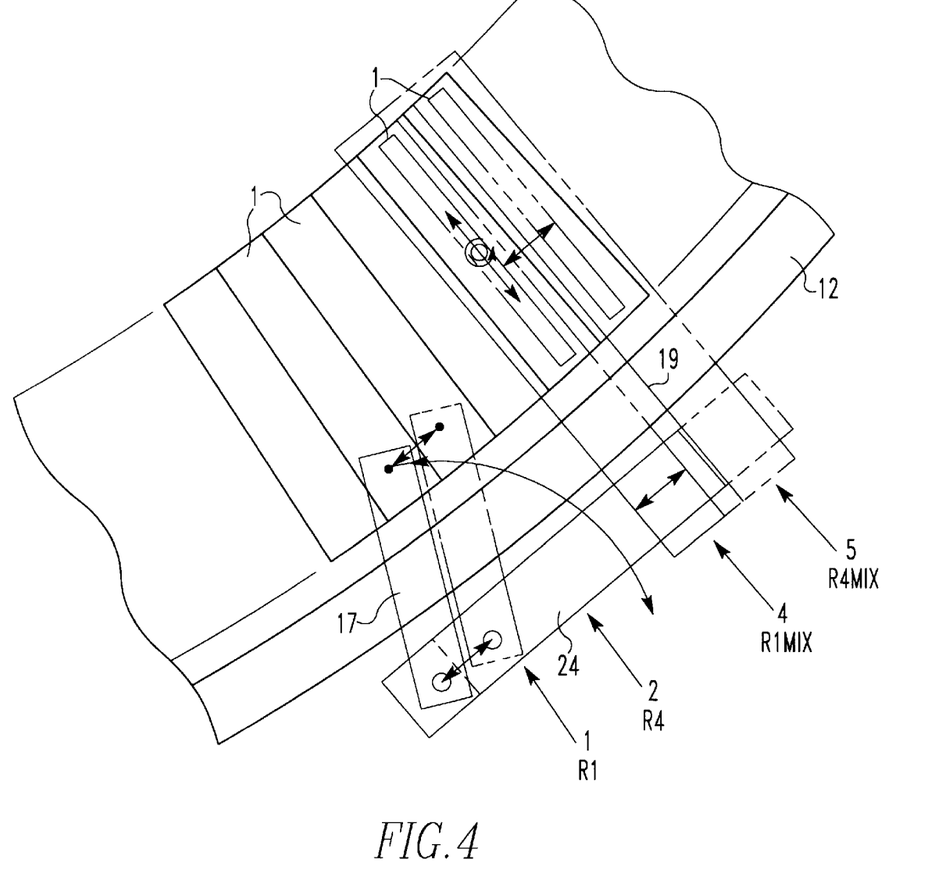
FIG. 4 is a view similar to FIG. 3, but showing another reagent pipette and another stirring device.

Referring next to FIG. 4, there is shown another reagent-injecting-and-stirring device for use with an automatic biochemical analyzer. FIG. 4 is a fragmentary enlarged view similar to FIG. 3.

In the embodiment shown in FIG. 3, the reagent pipette 17 is rotated so that it can inject aliquots of reagent into reaction containers 11 either at position 1 or at position 2. The stirring device 19 is linearly moved one pitch back and forth so that it can stir the liquid either at position 4 or at position 5. In the embodiment shown in FIG. 4, the reagent pipette 17 is rotated so that it can inject aliquots of reagent into the reaction containers 11 only at one position 1 or 2. However, the reagent pipette 17 can linearly move one pitch back and forth along the tangential line to the outer surface of the reaction turntable 12. In the embodiment shown in FIG. 4, the first reagent pipette 17 and the first reaction stirring device 19 are held to a common support base 24. Therefore, the reagent pipette 17 or 18 can move one pitch back and forth, together with the stirring device 19 or 20. The configuration of FIG. 4 can be applied to any timing scheme of reagent injection and stirring illustrated in Table I.

As can be understood from the description provided thus far, in an automatic biochemical analyzer in accordance with the present invention, the reaction turntable is rotated in M pitches in one step, it being noted that M and N (the total number of reaction containers on the reaction turntable) do not have any common factor. Two adjacent positions can be established as first and second reagent-injecting positions where the reagent pipette can inject aliquots of reagent into reaction containers. Also, two adjacent positions can be established as first and second stirring positions where a stirring device can stir liquid in reaction containers. One reagent pipette is moved between these two established first and second injecting positions. One stirring device is moved between these two established first and second stirring positions. Consequently, it is possible to inject two kinds of reagents with only one reagent pipette and one stirring device. Thus, the number of the components of the instrument can be reduced. This can lead to a decrease in the cost.

Furthermore, more kinds of reagents can be injected and stirred by dividing one stepwise movement into a former stepwise movement and a latter stepwise movement with at least one intervening halt period.

TABLE I

| Step | Time | Pos. | Job |
|---|---|---|---|
| 1 | −3.0 | 110 | |
| 1 | −3.0 | 1 | R1INJECT |
| 2 | 0.0 | 1 | |
| 2 | 0.0 | 113 | S |
| 3 | 3.0 | 113 | |
| 3 | 3.0 | 4 | R1MIX |
| 4 | 6.0 | 4 | |
| 5 | 9.0 | 116 | |
| 6 | 12.0 | 7 | |
| 7 | 15.0 | 119 | |
| 8 | 18.0 | 10 | |
| 9 | 21.0 | 122 | |
| 10 | 24.0 | 13 | |
| 11 | 27.0 | 125 | |
| 12 | 30.0 | 16 | |
| 13 | 33.0 | 128 | |
| 14 | 36.0 | 19 | |
| 15 | 39.0 | 131 | |

TABLE I-continued

| Step | Time | Pos. | Job |
|---|---|---|---|
| 16 | 42.0 | 22 | |
| 17 | 45.0 | 134 | |
| 18 | 48.0 | 25 | |
| 19 | 51.0 | 137 | |
| 20 | 54.0 | 28 | |
| 21 | 57.0 | 140 | |
| 22 | 60.0 | 31 | |
| 23 | 63.0 | 143 | |
| 24 | 66.0 | 34 | |
| 25 | 69.0 | 146 | |
| 25 | 69.0 | 37 | R2INJECT |
| 26 | 72.0 | 37 | |
| 27 | 75.0 | 149 | |
| 27 | 75.0 | 40 | R2MIX |
| 28 | 78.0 | 40 | |
| 29 | 81.0 | 152 | |
| 30 | 84.0 | 43 | |
| 31 | 87.0 | 155 | |
| 32 | 90.0 | 46 | |
| 33 | 93.0 | 158 | |
| 34 | 96.0 | 49 | |
| 35 | 99.0 | 161 | |
| 36 | 102.0 | 52 | |
| 37 | 105.0 | 164 | |
| 38 | 108.0 | 55 | |
| 39 | 111.0 | 167 | |
| 40 | 114.0 | 58 | |
| 41 | 117.0 | 170 | |
| 42 | 120.0 | 61 | |
| 43 | 123.0 | 173 | |
| 44 | 126.0 | 64 | |
| 45 | 129.0 | 176 | |
| 46 | 132.0 | 67 | |
| 47 | 135.0 | 179 | |
| 48 | 138.0 | 70 | |
| 49 | 141.0 | 182 | |
| 50 | 144.0 | 73 | |
| 51 | 147.0 | 185 | |
| 52 | 150.0 | 76 | |
| 53 | 153.0 | 188 | |
| 54 | 156.0 | 79 | |
| 55 | 159.0 | 191 | |
| 56 | 162.0 | 82 | |
| 57 | 165.0 | 194 | |
| 58 | 168.0 | 85 | |
| 59 | 171.0 | 197 | |
| 60 | 174.0 | 88 | |
| 61 | 177.0 | 200 | |
| 62 | 180.0 | 91 | |
| 63 | 183.0 | 203 | |
| 64 | 186.0 | 94 | |
| 65 | 189 | 206 | |
| 66 | 192.0 | 97 | |
| 67 | 195.0 | 209 | |
| 68 | 198.0 | 100 | |
| 69 | 201.0 | 212 | |
| 70 | 204.0 | 103 | |
| 71 | 207.0 | 215 | |
| 72 | 210.0 | 106 | |
| 73 | 213.0 | 218 | |
| 74 | 216.0 | 109 | |
| 75 | 219.0 | 221 | |
| 76 | 222.0 | 112 | |
| 77 | 225.0 | 3 | |
| 78 | 228.0 | 115 | |
| 79 | 231 | 6 | |
| 80 | 234.0 | 118 | |
| 81 | 237.0 | 9 | |
| 82 | 240.0 | 121 | |
| 83 | 243.0 | 12 | |
| 84 | 246.0 | 124 | |
| 85 | 249.0 | 15 | |
| 86 | 252.0 | 127 | |
| 87 | 255.0 | 18 | |
| 88 | 258.0 | 130 | |
| 89 | 261.0 | 21 | |
| 90 | 264.0 | 133 | |
| 91 | 267.0 | 24 | |
| 92 | 270.0 | 136 | |
| 93 | 273.0 | 27 | |
| 94 | 276.0 | 139 | |
| 95 | 279.0 | 30 | |
| 96 | 282.0 | 142 | |
| 97 | 285.0 | 33 | |
| 98 | 288.0 | 145 | |
| 98 | 288.0 | 36 | R3INJECT |
| 99 | 291.0 | 36 | |
| 100 | 294 | 148 | |
| 100 | 294.0 | 39 | R3MIX |
| 101 | 297.0 | 39 | |
| 102 | 300.0 | 151 | |
| 103 | 303.0 | 42 | |
| 104 | 306.0 | 154 | |
| 105 | 309.0 | 45 | |
| 106 | 312.0 | 157 | |
| 107 | 315.0 | 48 | |
| 108 | 318.0 | 160 | |
| 109 | 321.0 | 51 | |
| 110 | 324.0 | 163 | |
| 111 | 327.0 | 54 | |
| 112 | 330.0 | 166 | |
| 113 | 333.0 | 57 | |
| 114 | 336.0 | 169 | |
| 115 | 339.0 | 60 | |
| 116 | 342.0 | 172 | |
| 117 | 345.0 | 63 | |
| 118 | 348.0 | 175 | |
| 119 | 351.0 | 66 | |
| 120 | 354.0 | 178 | |
| 121 | 357.0 | 69 | |
| 122 | 360.0 | 181 | |
| 123 | 363.0 | 72 | |
| 124 | 366.0 | 184 | |
| 125 | 369.0 | 75 | |
| 126 | 372.0 | 187 | |
| 127 | 375.0 | 78 | |
| 128 | 378.0 | 190 | |
| 129 | 381.0 | 81 | |
| 130 | 384.0 | 193 | |
| 131 | 387.0 | 84 | |
| 132 | 390.0 | 196 | |
| 133 | 393.0 | 87 | |
| 134 | 396.0 | 199 | |
| 135 | 399.0 | 90 | |
| 136 | 402.0 | 202 | |
| 137 | 405.0 | 93 | |
| 138 | 408.0 | 205 | |
| 139 | 411.0 | 96 | |
| 140 | 414.0 | 208 | |
| 141 | 417.0 | 99 | |
| 142 | 420.0 | 211 | |
| 143 | 423.0 | 102 | |
| 144 | 426.0 | 214 | |
| 145 | 429.0 | 105 | |
| 146 | 432.0 | 217 | |
| 147 | 435.0 | 108 | |
| 148 | 438.0 | 220 | |
| 149 | 441.0 | 111 | |
| 149 | 441.0 | 2 | R4INJECT |
| 150 | 444.0 | 2 | |
| 151 | 447.0 | 114 | |
| 151 | 447.0 | 5 | R4MIX |
| 152 | 450.0 | 5 | |
| 153 | 453.0 | 117 | |
| 154 | 456.0 | 8 | |
| 155 | 459.0 | 120 | |
| 156 | 462.0 | 11 | |
| 157 | 465.0 | 123 | |
| 158 | 468.0 | 14 | |
| 159 | 471.0 | 126 | |
| 160 | 474.0 | 17 | |
| 161 | 477.0 | 129 | |
| 162 | 480.0 | 20 | |
| 163 | 483.0 | 132 | |

TABLE I-continued

| Step | Time | Pos. | Job |
|---|---|---|---|
| 164 | 486.0 | 23 | |
| 165 | 489.0 | 135 | |
| 166 | 492.0 | 26 | |
| 167 | 495.0 | 138 | |
| 168 | 498.0 | 29 | |
| 169 | 501.0 | 141 | |
| 170 | 504.0 | 32 | |
| 171 | 507.0 | 144 | |
| 172 | 510.0 | 35 | |
| 173 | 513.0 | 147 | |
| 174 | 516.0 | 38 | |
| 175 | 519.0 | 150 | |
| 176 | 522.0 | 41 | |
| 177 | 525.0 | 153 | |
| 178 | 528.0 | 44 | |
| 179 | 531.0 | 156 | |
| 180 | 534.0 | 47 | |
| 181 | 537.0 | 159 | |
| 182 | 540.0 | 50 | |
| 183 | 543.0 | 162 | |
| 184 | 546.0 | 53 | |
| 185 | 549.0 | 165 | |
| 186 | 552.0 | 56 | |
| 187 | 555.0 | 168 | |
| 188 | 558.0 | 59 | |
| 189 | 561.0 | 171 | |
| 190 | 564.0 | 62 | |
| 191 | 567.0 | 174 | |
| 192 | 570.0 | 65 | |
| 193 | 573.0 | 177 | |
| 194 | 576.0 | 68 | |
| 195 | 579.0 | 180 | |
| 196 | 582.0 | 71 | |
| 197 | 585.0 | 183 | |
| 198 | 588.0 | 74 | |
| 199 | 591.0 | 186 | |
| 200 | 594.0 | 77 | |
| 201 | 597.0 | 189 | |
| 201 | 597.0 | 80 | WD1 |
| 202 | 600.0 | 80 | |
| 203 | 603.0 | 192 | |
| 203 | 603.0 | 83 | WD2 |
| 204 | 606.0 | 83 | |
| 205 | 609.0 | 195 | |
| 205 | 609.0 | 86 | WD3 |
| 206 | 612.0 | 86 | |
| 207 | 615.0 | 198 | |
| 207 | 615.0 | 89 | WD4 |
| 208 | 618.0 | 89 | |
| 209 | 621.0 | 201 | |
| 209 | 621.0 | 92 | WD5 |
| 210 | 624.0 | 92 | |
| 211 | 627.0 | 204 | |
| 211 | 627.0 | 95 | WD6 |
| 212 | 630.0 | 95 | |
| 213 | 633.0 | 207 | |
| 214 | 636.0 | 98 | CB1 |
| 215 | 639.0 | 210 | |
| 216 | 642.0 | 101 | CB2 |
| 217 | 645.0 | 213.0 | |
| 217 | 645.0 | 104 | WD7 |
| 218 | 648.0 | 104 | |
| 219 | 651.0 | 216 | |
| 219 | 651.0 | 107 | WD8 |
| 220 | 654.0 | 107 | |
| 221 | 657.0 | 219 | |

TABLE II

| Step | Time | Pos. | Job |
|---|---|---|---|
| 1 | −4.5 | 155 | |
| 1 | −4.5 | 1 | R1INJECT |
| 1 | −4.5 | 1 | |

TABLE II-continued

| Step | Time | Pos. | Job |
|---|---|---|---|
| 2 | 0.0 | 46 | |
| 2 | 0.0 | 113 | SAMPLE INJECT |
| 2 | 0.0 | 113 | |
| 3 | 4.5 | 158 | |
| 3 | 4.5 | 4 | R1MIX |
| 3 | 4.5 | 4 | |
| 4 | 9.0 | 49 | |
| 4 | 9.0 | 116 | |
| 5 | 13.5 | 161 | |
| 5 | 13.5 | 7 | |
| 6 | 18.0 | 52 | |
| 6 | 18.0 | 119 | |
| 7 | 22.5 | 164 | |
| 7 | 22.5 | 10 | |
| 8 | 27.0 | 55 | |
| 8 | 27.0 | 122 | |
| 9 | 31.5 | 167 | |
| 9 | 31.5 | 13 | |
| 10 | 36.0 | 58 | |
| 10 | 36.0 | 125 | |
| 11 | 40.5 | 170 | |
| 11 | 40.5 | 16 | |
| 12 | 45.0 | 61 | |
| 12 | 45.0 | 128 | |
| 13 | 49.5 | 173 | |
| 13 | 49.5 | 19 | |
| 14 | 54.0 | 64 | |
| 14 | 54.0 | 131 | |
| 15 | 58.5 | 176 | |
| 15 | 58.5 | 22 | |
| 16 | 63.0 | 67 | |
| 16 | 63.0 | 134 | |
| 17 | 67.5 | 179 | |
| 17 | 67.5 | 25 | |
| 18 | 72.0 | 70 | |
| 18 | 72.0 | 137 | |
| 19 | 76.5 | 182 | |
| 19 | 76.5 | 28 | |
| 20 | 81.0 | 73 | |
| 20 | 81.0 | 140 | |
| 21 | 85.5 | 185 | |
| 21 | 85.5 | 31 | |
| 22 | 90.0 | 76 | |
| 22 | 90.0 | 143 | |
| 23 | 94.5 | 188 | |
| 23 | 94.5 | 34 | |
| 24 | 99.0 | 79 | |
| 24 | 99.0 | 146 | |
| 25 | 103.5 | 191 | |
| 25 | 103.5 | 37 | R2INJECT |
| 25 | 103.5 | 37 | |
| 26 | 108.0 | 82 | |
| 26 | 108.0 | 149 | |
| 27 | 112.5 | 194 | |
| 27 | 112.5 | 40 | R2MIX |
| 27 | 112.5 | 40 | |
| 28 | 117.0 | 85 | |
| 28 | 117.0 | 152 | |
| 29 | 121.5 | 197 | |
| 29 | 121.5 | 43 | |
| 30 | 126.0 | 88 | |
| 30 | 126.0 | 155 | |
| 31 | 130.5 | 200 | |
| 31 | 130.5 | 46 | |
| 32 | 135.0 | 91 | |
| 32 | 135.0 | 158 | |
| 33 | 139.5 | 203 | |
| 33 | 139.5 | 49 | |
| 34 | 144.0 | 94 | |
| 34 | 144.0 | 161 | |
| 35 | 148.5 | 206 | |
| 35 | 148.5 | 52 | |
| 36 | 153.0 | 97 | |
| 36 | 153.0 | 164 | |
| 37 | 157.5 | 209 | |
| 37 | 157.5 | 55 | |
| 38 | 162.0 | 100 | |

TABLE II-continued

| Step | Time | Pos. | Job |
|---|---|---|---|
| 38 | 162.0 | 167 | |
| 39 | 166.5 | 212 | |
| 39 | 166.5 | 58 | |
| 40 | 171.0 | 103 | |
| 40 | 171.0 | 170 | |
| 41 | 175.5 | 215 | |
| 41 | 175.5 | 61 | |
| 42 | 180.0 | 106 | |
| 42 | 180.0 | 173 | |
| 43 | 184.5 | 218 | |
| 43 | 184.5 | 64 | |
| 44 | 189.0 | 109 | |
| 44 | 189.0 | 176 | |
| 45 | 193.5 | 221 | |
| 45 | 193.5 | 67 | |
| 46 | 198.0 | 112 | |
| 46 | 198.0 | 179 | |
| 47 | 202.5 | 3 | |
| 47 | 202.5 | 70 | |
| 48 | 207.0 | 115 | |
| 48 | 207.0 | 182 | |
| 49 | 211.5 | 6 | |
| 49 | 211.5 | 73 | |
| 50 | 216.0 | 118 | |
| 50 | 216.0 | 185 | |
| 51 | 220.5 | 9 | |
| 51 | 220.5 | 76 | |
| 52 | 225.0 | 121 | |
| 52 | 225.0 | 188 | |
| 53 | 229.5 | 12 | |
| 53 | 229.5 | 79 | |
| 54 | 234.0 | 124 | |
| 54 | 234.0 | 191 | |
| 55 | 238.5 | 15 | |
| 55 | 238.5 | 82 | |
| 56 | 243.0 | 127 | |
| 56 | 243.0 | 194 | |
| 57 | 247.5 | 18 | |
| 57 | 247.5 | 85 | |
| 58 | 252.0 | 130 | |
| 58 | 252.0 | 197 | |
| 59 | 256.5 | 21 | |
| 59 | 256.5 | 88 | |
| 60 | 261.0 | 133 | |
| 60 | 261.0 | 200 | |
| 61 | 265.5 | 24 | |
| 61 | 265.5 | 91 | |
| 62 | 270.0 | 136 | |
| 62 | 270.0 | 203 | |
| 63 | 274.5 | 27 | |
| 63 | 274.5 | 94 | |
| 64 | 279.0 | 139 | |
| 64 | 279.0 | 206 | |
| 65 | 283.5 | 30 | |
| 65 | 283.5 | 97 | |
| 66 | 288.0 | 142 | |
| 66 | 288.0 | 209 | |
| 67 | 292.5 | 33 | |
| 67 | 292.5 | 100 | |
| 68 | 297.0 | 145 | |
| 68 | 297.0 | 212 | |
| 68 | 297.0 | 36 | R3 (45) INJECT |
| 69 | 301.5 | 36 | |
| 69 | 301.5 | 103 | |
| 70 | 306.0 | 148 | |
| 70 | 306.0 | 215 | |
| 70 | 306.0 | 39 | R3MIX (45) |
| 71 | 310.5 | 39 | |
| 71 | 310.5 | 106 | |
| 72 | 315.0 | 151 | |
| 72 | 315.0 | 218 | |
| 73 | 319.5 | 42 | |
| 73 | 319.5 | 109 | |
| 74 | 324.0 | 154 | |
| 74 | 324.0 | 221 | |
| 75 | 328.5 | 45 | |
| 75 | 328.5 | 112 | |
| 76 | 333.0 | 157 | |
| 76 | 333.0 | 3 | |
| 77 | 337.5 | 48 | |
| 77 | 337.5 | 115 | |
| 78 | 342.0 | 160 | |
| 78 | 342.0 | 6 | |
| 79 | 346.5 | 51 | |
| 79 | 346.5 | 118 | |
| 80 | 351.0 | 163 | |
| 80 | 351.0 | 9 | |
| 81 | 355.5 | 54 | |
| 81 | 355.5 | 121 | |
| 82 | 360.0 | 166 | |
| 82 | 360.0 | 12 | |
| 83 | 364.5 | 57 | |
| 83 | 364.5 | 124 | |
| 84 | 369.0 | 169 | |
| 84 | 369.0 | 15 | |
| 85 | 373.5 | 60 | |
| 85 | 373.5 | 127 | |
| 86 | 378.0 | 172 | |
| 86 | 378.0 | 18 | |
| 87 | 382.5 | 63 | |
| 87 | 382.5 | 130 | |
| 88 | 387.0 | 175 | |
| 88 | 387.0 | 21 | |
| 89 | 391.5 | 66 | |
| 89 | 391.5 | 133 | |
| 90 | 396.0 | 178 | |
| 90 | 396.0 | 24 | |
| 91 | 400.5 | 69 | |
| 91 | 400.5 | 136 | |
| 92 | 405.0 | 181 | |
| 92 | 405.0 | 27 | |
| 93 | 409.5 | 72 | |
| 93 | 409.5 | 139 | |
| 94 | 414.0 | 184 | |
| 94 | 414.0 | 30 | |
| 95 | 418.5 | 75 | |
| 95 | 418.5 | 142 | |
| 96 | 423.0 | 187 | |
| 96 | 423.0 | 33 | |
| 97 | 427.5 | 78 | |
| 97 | 427.5 | 145 | |
| 98 | 432.0 | 190 | |
| 98 | 432.0 | 36 | |
| 99 | 436.5 | 81 | |
| 99 | 436.5 | 148 | |
| 100 | 441.0 | 193 | |
| 100 | 441.0 | 39 | |
| 101 | 445.5 | 84 | |
| 101 | 445.5 | 151 | |
| 102 | 450.0 | 196 | |
| 102 | 450.0 | 42 | |
| 103 | 454.5 | 87 | |
| 103 | 454.5 | 154 | |
| 104 | 459.0 | 199 | |
| 104 | 459.0 | 45 | |
| 105 | 463.5 | 90 | |
| 105 | 463.5 | 157 | |
| 106 | 468.0 | 202 | |
| 106 | 468.0 | 48 | |
| 107 | 472.5 | 93 | |
| 107 | 472.5 | 160 | |
| 108 | 477.0 | 205 | |
| 108 | 477.0 | 51 | |
| 109 | 481.5 | 96 | |
| 109 | 481.5 | 163 | |
| 110 | 486.0 | 208 | |
| 110 | 486.0 | 54 | |
| 111 | 490.5 | 99 | |
| 111 | 490.5 | 166 | |
| 112 | 495.0 | 211 | |
| 112 | 495.0 | 57 | |
| 113 | 499.5 | 102 | |
| 113 | 499.5 | 169 | |
| 114 | 504.0 | 214 | |

TABLE II-continued

| Step | Time | Pos. | Job |
|---|---|---|---|
| 114 | 504.0 | 60 | |
| 115 | 508.5 | 105 | |
| 115 | 508.5 | 172 | |
| 116 | 513.0 | 217 | |
| 116 | 513.0 | 63 | |
| 117 | 517.5 | 108 | |
| 117 | 517.5 | 175 | |
| 118 | 522.0 | 220 | |
| 118 | 522.0 | 66 | |
| 119 | 526.5 | 111 | |
| 119 | 526.5 | 178 | |
| 119 | 526.5 | 2 | R4 (45) INJECT |
| 120 | 531.0 | 2 | |
| 120 | 531.0 | 69 | |
| 121 | 535.5 | 114 | |
| 121 | 535.5 | 181 | |
| 121 | 535.5 | 5 | R4MIX |
| 122 | 540.0 | 5 | |
| 122 | 540.0 | 72 | |
| 123 | 544.5 | 117 | |
| 123 | 544.5 | 184 | |
| 124 | 549.0 | 8 | |
| 124 | 549.0 | 75 | |
| 125 | 553.5 | 120 | |
| 125 | 553.5 | 187 | |
| 126 | 558.0 | 11 | |
| 126 | 558.0 | 78 | |
| 127 | 562.5 | 123 | |
| 127 | 562.5 | 190 | |
| 128 | 567.0 | 14 | |
| 128 | 567.0 | 81 | |
| 129 | 571.5 | 126 | |
| 129 | 571.5 | 193 | |
| 130 | 576.0 | 17 | |
| 130 | 576.0 | 84 | |
| 131 | 580.5 | 129 | |
| 131 | 580.5 | 196 | |
| 132 | 585.0 | 20 | |
| 132 | 585.0 | 87 | |
| 133 | 589.5 | 132 | |
| 133 | 589.5 | 199 | |
| 134 | 594.0 | 23 | |
| 134 | 594.0 | 90 | |
| 135 | 598.5 | 135 | |
| 135 | 598.5 | 202 | |
| 136 | 603.0 | 26 | |
| 136 | 603.0 | 93 | |
| 137 | 607.5 | 138 | |
| 137 | 607.5 | 205 | |
| 138 | 612.0 | 29 | |
| 138 | 612.0 | 96 | |
| 139 | 616.5 | 141 | |
| 139 | 616.5 | 208 | |
| 140 | 621.0 | 32 | |
| 140 | 621.0 | 99 | |
| 141 | 625.5 | 144 | |
| 141 | 625.5 | 211 | |
| 142 | 630.0 | 35 | |
| 142 | 630.0 | 102 | |
| 143 | 634.5 | 147 | |
| 143 | 634.5 | 214 | |
| 144 | 639.0 | 38 | |
| 144 | 639.0 | 104 | |
| 145 | 643.5 | 150 | |
| 145 | 643.5 | 217 | |
| 146 | 648.0 | 41 | |
| 146 | 648.0 | 108 | |
| 147 | 652.5 | 153 | |
| 147 | 652.5 | 220 | |
| 148 | 657.0 | 44 | |
| 148 | 657.0 | 111 | |
| 149 | 661.5 | 156 | |
| 149 | 661.5 | 2 | |
| 150 | 666.0 | 47 | |
| 150 | 666.0 | 114 | |
| 151 | 670.5 | 159 | |
| 151 | 670.5 | 5 | |
| 152 | 675.0 | 50 | |
| 152 | 675.0 | 117 | |
| 153 | 679.5 | 162 | |
| 153 | 679.5 | 8 | |
| 154 | 684.0 | 53 | |
| 154 | 684.0 | 120 | |
| 155 | 688.5 | 165 | |
| 155 | 688.5 | 11 | |
| 156 | 693.0 | 56 | |
| 156 | 693.0 | 123 | |
| 157 | 697.5 | 168 | |
| 157 | 697.5 | 14 | |
| 158 | 702.0 | 59 | |
| 158 | 702.0 | 126 | |
| 159 | 706.5 | 171 | |
| 159 | 706.5 | 17 | |
| 160 | 711.0 | 62 | |
| 160 | 711.0 | 129 | |
| 161 | 715.5 | 174 | |
| 161 | 715.5 | 20 | |
| 162 | 720.0 | 65 | |
| 162 | 720.0 | 132 | |
| 163 | 724.5 | 177 | |
| 163 | 724.5 | 23 | |
| 164 | 729.0 | 68 | |
| 164 | 729.0 | 135 | |
| 165 | 733.5 | 180 | |
| 165 | 733.5 | 26 | |
| 166 | 738.0 | 71 | |
| 166 | 738.0 | 138 | |
| 167 | 742.5 | 183 | |
| 167 | 742.5 | 29 | |
| 168 | 747.0 | 74 | |
| 168 | 747.0 | 141 | |
| 169 | 751.5 | 186 | |
| 169 | 751.5 | 32 | |
| 170 | 756.0 | 77 | |
| 170 | 756.0 | 144 | |
| 171 | 760.5 | 189 | |
| 171 | 760.5 | 35 | |
| 172 | 765.0 | 80 | |
| 172 | 765.0 | 147 | |
| 173 | 769.5 | 192 | |
| 173 | 769.5 | 38 | |
| 174 | 774.0 | 83 | |
| 174 | 774.0 | 150 | |
| 175 | 778.5 | 195 | |
| 175 | 778.5 | 41 | |
| 176 | 783.0 | 86 | |
| 176 | 783.0 | 153 | |
| 177 | 787.5 | 198 | |
| 177 | 787.5 | 44 | |
| 178 | 792.0 | 89 | |
| 178 | 792.0 | 156 | |
| 179 | 796.5 | 201 | |
| 179 | 796.5 | 47 | |
| 180 | 801.0 | 92 | |
| 180 | 801.0 | 159 | |
| 181 | 805.5 | 204 | |
| 181 | 805.5 | 50 | |
| 182 | 810.0 | 95 | |
| 182 | 810.0 | 162 | |
| 183 | 814.5 | 207 | |
| 183 | 814.5 | 53 | |
| 184 | 819.0 | 98 | |
| 184 | 819.0 | 165 | |
| 185 | 823.5 | 210 | |
| 185 | 823.5 | 56 | |
| 186 | 828.0 | 101 | |
| 186 | 828.0 | 168 | |
| 187 | 832.5 | 213 | |
| 187 | 832.5 | 59 | |
| 188 | 837.0 | 104 | |
| 188 | 837.0 | 171 | |
| 189 | 841.5 | 216 | |
| 189 | 841.5 | 62 | |
| 190 | 846.0 | 107 | |

TABLE II-continued

| Step | Time | Pos. | Job |
|---|---|---|---|
| 190 | 846.0 | 174 | |
| 191 | 850.5 | 219 | |
| 191 | 850.5 | 65 | |
| 192 | 855.0 | 110 | |
| 192 | 855.0 | 177 | |
| 193 | 859.5 | 1 | |
| 193 | 859.5 | 68 | |
| 194 | 864.0 | 113 | |
| 194 | 864.0 | 180 | |
| 195 | 868.5 | 4 | |
| 195 | 868.5 | 71 | |
| 196 | 873.0 | 116 | |
| 196 | 873.0 | 183 | |
| 197 | 877.5 | 7 | |
| 197 | 877.5 | 74 | |
| 198 | 882.0 | 119 | |
| 198 | 882.0 | 186 | |
| 199 | 886.5 | 10 | |
| 199 | 886.5 | 77 | |
| 200 | 891.0 | 122 | |
| 200 | 891.0 | 189 | |
| 201 | 895.5 | 13 | |
| 201 | 895.5 | 80 | WD1 |
| 201 | 895.5 | 80 | |
| 202 | 900.0 | 125 | |
| 202 | 900.0 | 192 | |
| 203 | 904.5 | 16 | |
| 203 | 904.5 | 83 | WD2 |
| 203 | 904.5 | 83 | |
| 204 | 909.0 | 128 | |
| 204 | 909.0 | 195 | |
| 205 | 913.5 | 19 | |
| 205 | 913.5 | 86 | WD3 |
| 205 | 913.5 | 86 | |
| 206 | 918.0 | 131 | |
| 206 | 918.0 | 198 | |
| 207 | 922.5 | 22 | |
| 207 | 922.5 | 89 | WD4 |
| 207 | 922.5 | 89 | |
| 208 | 927.0 | 134 | |
| 208 | 927.0 | 201 | |
| 209 | 931.5 | 25 | |
| 209 | 931.5 | 92 | WD5 |
| 209 | 931.5 | 92 | |
| 210 | 936.0 | 137 | |
| 210 | 936.0 | 204 | |
| 211 | 940.5 | 28 | |
| 211 | 940.5 | 95 | WD6 |
| 211 | 940.5 | 95 | |
| 212 | 945.0 | 140 | |
| 212 | 945.0 | 207 | |
| 213 | 949.5 | 31 | |
| 213 | 949.5 | 98 | |
| 214 | 954.0 | 143 | CB1 |
| 214 | 954.0 | 210 | |
| 215 | 958.5 | 34 | |
| 215 | 958.5 | 101 | |
| 216 | 963.0 | 146 | CB2 |
| 216 | 963.0 | 213 | |
| 217 | 967.5 | 37 | |
| 217 | 967.5 | 104 | WD7 |
| 217 | 967.5 | 104 | |
| 218 | 972.0 | 149 | |
| 218 | 972.0 | 216 | |
| 219 | 976.5 | 40 | |
| 219 | 976.5 | 107 | WD8 |
| 219 | 976.5 | 107 | |
| 220 | 981.0 | 152 | |
| 220 | 981.0 | 219 | |
| 221 | 985.5 | 43 | |
| 221 | 985.5 | 110 | |

What is claimed is:

1. An automatic biochemical analyzer comprising:

a sample turntable on which a plurality of sample containers for holding samples is arrayed;

a diluting turntable having diluting containers arranged therein;

a diluting pipette for drawing in a sample from one of said sample containers and discharging said sample into said diluting containers together with a diluent;

a reaction turntable on which a plurality of reaction containers being N in number is substantially regularly spaced from each other by one pitch circumferentially, said reaction turntable being rotated in M pitches at a time, said M and said N being so selected that they do not have any common factor;

a reagent turntable on which a plurality of reagent containers for holding reagents is arrayed;

a sampling pipette for drawing in a diluted sample aliquot from a selected one of said diluting containers and injecting the drawn diluted sample aliquot into a selected one of said reaction containers;

a reagent pipette for drawing in an aliquot of a selected one of said reagents and injecting the drawn reagent aliquot into said selected reaction container at any one of first and second injecting positions adjacent to each other;

a stirring device for stirring said diluted sample aliquot and said reagent aliquot in said selected reagent container at any one of first and second stirring positions adjacent to each other, said stirring device being capable of moving between said first and second stirring positions, said first and second injecting positions and said first and second stirring positions being different; and a detector for detecting reaction products arising from said diluted sample aliquot and said reagent aliquot after the stirring.

2. The automatic biochemical analyzer of claim 1, wherein when said reaction turntable is rotated in M pitches in one step, said reaction turntable is first rotated in a former operative period corresponding to an earlier intermediate number of pitches, halted for a given period of time, and then rotated in a latter operative period corresponding to a latter number of remaining pitches.

3. The automatic biochemical analyzer of claim 1, wherein said reagent pipette can be moved between said first and second injecting positions.

4. The automatic biochemical analyzer of claim 3, wherein said reagent pipette is moved one pitch between said first and second injecting positions and said stirring device is moved one pitch between said first and second stirring positions by a common driving mechanism.

5. The automatic biochemical analyzer of claim 1, wherein third and fourth injecting positions adjacent to each other and independent of said first and second injecting positions are established as injecting positions where a second reagent pipette injects a reagent into said selected reaction container, and wherein third and fourth stirring positions adjacent to each other and independent of said first and second stirring positions are established as stirring positions where a second stirring device stirs liquids in said selected reaction container, said second stirring device being capable of moving between said third and fourth stirring positions.

6. The automatic biochemical analyzer of claim 5, wherein said second reagent pipette can be moved between said third and fourth injecting positions.

7. The automatic biochemical analyzer of claim 2, wherein third and fourth injecting positions adjacent to each other and independent of said first and second injecting positions are established as injecting positions where a second reagent pipette injects a reagent into said selected reaction container, and wherein third and fourth stirring positions adjacent to each other and independent of said first and second stirring positions are established as stirring positions where a second stirring device stirs liquids in said selected reaction container, said second stirring device being capable of moving between said third and fourth stirring positions.

8. The automatic biochemical analyzer of claim 4, wherein third and fourth injecting positions adjacent to each other and independent of said first and second injecting positions are established as injecting positions where a second reagent pipette injects a reagent into said selected reaction container, and wherein third and fourth stirring positions adjacent to each other and independent of said first and second stirring positions are established as stirring positions where a second stirring device stirs liquids in said selected reaction container, said second stirring device being capable of moving between said third and fourth stirring positions.

\* \* \* \* \*

UNITED STATES PATENT AND TRADEMARK OFFICE
CERTIFICATE OF CORRECTION

PATENT NO. : 6,146,592  
DATED : November 14, 2000  
INVENTOR(S) : Kiyoshi Kawashima et al.

Page 1 of 1

It is certified that error appears in the above-identified patent and that said Letters Patent is hereby corrected as shown below:

Title Page, insert:  
--(30) Foreign Application Priority Data  
Aug. 21, 1996      (JP)...............8-219739--.

Title Page, under (56) References Cited, U.S. PATENT DOCUMENTS, insert:
--4,908,320    3/1990    Zakowski et al...................436/45
5,037,612    8/1991    Takahashi et al..................422/64
5,212,094    5/1993    Ogawa...........................436/47
5,320,966    6/1994    Mitsumaki et al.................436/47
5,352,612    10/1994    Huber et al.....................436/47--.

Column 1,  
Line 54, "of he" should read --of the--.

Signed and Sealed this

Third Day of July, 2001

Attest:

NICHOLAS P. GODICI  
*Attesting Officer*      *Acting Director of the United States Patent and Trademark Office*